United States Patent
Benni et al.

(10) Patent No.: US 8,897,848 B2
(45) Date of Patent: Nov. 25, 2014

(54) APPARATUS AND METHOD FOR NON-INVASIVELY DETERMINING OXYGEN SATURATION OF VENOUS BLOOD AND CARDIAC OUTPUT USING NIRS

(75) Inventors: Paul B. Benni, Acton, MA (US); Suzanne M. Carroll, Norwich, CT (US)

(73) Assignee: CAS Medical Systems, Inc., Branford, CT (US)

( * ) Notice: Subject to any disclaimer, the term of this patent is extended or adjusted under 35 U.S.C. 154(b) by 469 days.

(21) Appl. No.: 13/228,183

(22) Filed: Sep. 8, 2011

(65) Prior Publication Data

US 2012/0065485 A1    Mar. 15, 2012

Related U.S. Application Data

(60) Provisional application No. 61/380,931, filed on Sep. 8, 2010.

(51) Int. Cl.
*A61B 5/1455* (2006.01)

(52) U.S. Cl.
CPC ......... *A61B 5/14551* (2013.01); *A61B 5/14553* (2013.01)
USPC .......................................... 600/323; 600/324

(58) Field of Classification Search
USPC .................................................. 600/310–344
See application file for complete search history.

(56) References Cited

U.S. PATENT DOCUMENTS

| 4,949,724 A * | 8/1990 | Mahutte et al. ............... 600/526 |
| 6,456,862 B2 * | 9/2002 | Benni ............................ 600/331 |

* cited by examiner

*Primary Examiner* — Eric Winakur
*Assistant Examiner* — Marjan Fardanesh
(74) *Attorney, Agent, or Firm* — O'Shea Getz P.C.

(57) ABSTRACT

A method and apparatus for determining a venous oxygen saturation value (SvO2) of a subject is provided. The method includes the steps of: a) sensing a plurality of tissue regions on a subject using a NIRS oximeter adapted to determine a tissue oxygen saturation value (StO2) for each region, each region independent of the other regions and each region sensed using a NIRS oximeter sensor specific to that region, and determining a StO2 value for that region; b) assigning a coefficient to each region, each of which coefficients reflects a portion of the StO2 value for the region attributable to a composite venous blood return representative of the tissue regions measured; and c) determining a composite SvO2 value for the subject using the StO2 region values and the respective coefficients.

19 Claims, 2 Drawing Sheets

APPARATUS AND METHOD FOR NON-INVASIVELY DETERMINING OXYGEN SATURATION OF VENOUS BLOOD AND CARDIAC OUTPUT USING NIRS

Applicant hereby claims priority benefits under 35 U.S.C. §119(e) of U.S. Provisional Patent Application No. 61/380,931 filed Sep. 8, 2010, the disclosure of which is herein incorporated by reference.

BACKGROUND OF THE INVENTION

1. Technical Field

The present invention relates to apparatus and methods for non-invasively determining oxygen saturation in blood in general, and to apparatus and methods for non-invasively determining oxygen saturation in venous blood in particular.

2. Background Information

Arterial blood oxygen saturation ($SaO_2$) can be determined by pulse oximetry or co-oximetry measurements of arterial blood. Pulse oximetry, for example, is a well established non-invasive technique for determining a $SaO_2$ value. Most subjects have a $SaO_2$ value in the range of 95-100%. Central venous blood oxygen saturation (ScvO2) and mixed venous blood oxygen saturation (SmvO2), both types of composite venous blood oxygen saturation (SvO2), are measurements of the relationship between oxygen consumption and oxygen delivery in the body. Normal values of mixed venous oxygen saturation (SmvO2) are 60-80% $O_2$ saturation. Central venous oxygen saturation (ScvO2) values represent regional venous saturations with a normal value of about 70% and historically have been measured invasively just outside the heart, usually in the superior vena cava (SVC). ScvO2 usually measures slightly higher than SmvO2 as it has not mixed with the venous blood from the coronary sinus draining into the right atrium. Although the values may differ, they trend together.

Mixed venous oxygen saturation ($SmvO_2$) is far more difficult to determine than arterial blood oxygen saturation (SaO2). Pulmonary artery saturation is an accurate indicator of SmvO2. The pulmonary artery blood includes venous blood returning to the heart via the superior vena cava (SVC) and via the inferior vena cava (IVC). From there, blood enters the right atrium and into the right ventricle where it is mixed. Since the SVC and IVC oxygen saturations can be different, the resultant oxygen saturation in the right ventricle and into the pulmonary artery is a mixed value likely between SVC and IVC oxygen saturations. However, obtaining a pulmonary artery blood oxygen saturation value or right ventricle oxygen saturation value is difficult and must be done invasively; e.g., requires a catheter be placed to access these sites.

Accurately determining the adequacy of tissue oxygenation in critically ill patients can be vital to patient treatment. Tissue hypoxia or imbalances between whole-body oxygen supply and demand can occur even when the subject has normal blood pressure, central venous pressure, heart rate, and blood gas values. It is desirable, therefore, to have more direct indicators of tissue oxygen saturation; e.g., mixed and central venous oxygen saturations.

A normal cardiovascular response of increasing oxygen consumption (VO2) is to increase O2 extraction from the blood and/or increase cardiac output (CO). Oxygen consumption is typically independent of oxygen delivery (DO2), since tissues can satisfy oxygen requirements by increasing O2 extraction when DO2 decreases. However, once a critical DO2 compensatory increase in O2 extraction is reached, the ability to satisfy oxygen consumption is dependent on DO2. If oxygen consumption requirements cannot be met, then tissue hypoxia can occur.

A decrease in SmvO2 and ScvO2 can represent an increased metabolic stress. For example, metabolic stress can occur if DO2 does not increase in such a way to cover an increased VO2, or if DO2 drops because of decrease in either arterial O2 content, cardiac output, or both. The magnitude of the decrease indicates the extent to which the physiological reserves are stressed:

| | |
|---|---|
| SmvO2 > 75% | Normal Extraction: O2 supply > O2 demand |
| 75% > SmvO2 > 50% | Compensatory Extraction: Increase in O2 demand, or decrease in O2 supply |
| 50% > SmvO2 > 30% | Exhaustion of Extraction; beginning of lactic acidosis; O2 supply < O2 demand |
| 30% > SmvO2 > 25% | Severe lactic acidosis |
| SmvO2 < 25% | Cellular death |

The cardiocirculatory system may be challenged by a drop in DO2 that is induced by anemia, hypoxia, hypovolemia, or heart failure. Fever, pain, or stress can also decrease SmvO2 or ScvO2 by increasing whole-body VO2.

Historically, mixed venous oxygen saturation (SmvO2) values have been invasively obtained using a pulmonary artery catheter, and central venous oxygen saturation (ScvO2) values have been invasively obtained using a central venous catheter. The ScvO2 value reflects the degree of oxygen extraction from the brain and the upper part of the body. The SmvO2 value reflects the relationship between whole-body O2 consumption and cardiac output.

A central venous blood sampling (e.g., from the superior vena cava) reflects the venous blood of the upper body but neglects venous blood from the lower body (i.e., intra-abdominal organs). Venous O2 saturation values can differ among several organ systems since the organs extract different amounts of O2. ScvO2 is usually less than SmvO2 by about 2-3% because the lower body extracts less O2 than the upper body, making inferior vena cava O2 saturation higher. The primary cause of the lower O2 extraction is that many of the vascular circuits that drain into the inferior vena cava use blood flow for nonoxidative phosphorylation needs (e.g., renal blood flow, portal flow, hepatic blood flow, etc.). However, SmvO2 and ScvO2 change similarly when the whole body ratio of O2 supply to demand is altered.

The difference between the absolute value of ScvO2 and SmvO2 can change, however, when the patient is in shock. In septic shock, ScvO2 often exceeds SmvO2 by about 8%. During cardiogenic or hypovolemic shock, mesenteric and renal blood flow decreases and an increase in O2 extraction in these organs typically follows. During septic shock, regional O2 consumption of the gastrointestinal tract (and therefore regional O2 extraction) increases despite elevated regional blood flows. On the other hand, cerebral blood flow is maintained over some period in shock. This characteristic can cause a delayed drop of ScvO2 in comparison to SmvO2, and the correlation between these two parameters could worsen as a result. It should be noted, however, that venous oximetry can provide accurate information on the adequacy of tissue oxygenation only if the tissue is still capable of extracting O2. In the case of arteriovenous shunting on the microcirculatory level or cell death, SmvO2 and ScvO2 may not decrease or may even show elevated values despite severe tissue hypoxia; e.g., patients with prolonged cardiac arrest have experienced venous hyperoxia, despite test results showing a ScvO2 higher than 80% which is indicative of impaired oxygen use.

The ability to determine a composite venous oxygen saturation value (SvO2) can facilitate the determination of other information, such as the cardiac output of a subject. The Fick Principle provides that blood flow to an organ can be calculated using a marker substance if the following information is known: a) the amount of marker substance taken up by the organ per unit time; b) the concentration of the marker substance in the arterial blood supplying the organ; and c) the concentration of the marker substance in venous blood leaving the organ. Using Fick's original method, the cardiac output ("CO") of a subject could be measured by determining the oxygen consumption ("VO$_2$"), the oxygen content of the blood taken from the pulmonary artery ("Cv"; i.e., mixed venous blood), and the oxygen content of the blood from a peripheral artery ("Ca"; i.e., arterial blood). The VO$_2$ could be determined using a spirometer within a closed rebreathing circuit incorporating a CO$_2$ absorber. The Ca and Cv values could be determined by evaluating blood samples invasively taken from the subject. From these values, the VO$_2$ can be expressed as:

$$VO_2 = (CO \times C_a) - (CO \times C_v) \quad \text{(Eqn. 1)}$$

The above relationship can be manipulated as follows:

$$CO = \frac{VO_2}{C_a - C_v} \quad \text{(Eqn. 2)}$$

and the cardiac output calculated. In reality, however, this method is impractical and rarely used due to the difficulty of collecting and analyzing the O$_2$ concentrations within the sample.

What is needed is an apparatus and method that can be used to determine the oxygen saturation of venous blood (SvO2) at any location within a subject's body, and one that can be specifically used to non-invasively determine a mixed venous oxygen saturation value (SmvO2) and a central venous oxygen saturation (ScvO2) value.

SUMMARY OF THE INVENTION

According to an aspect of the present invention, a method for determining a composite venous oxygen saturation value (SvO2) of a subject is provided. The method includes the steps of: a) sensing a plurality of tissue regions on a subject using a NIRS oximeter adapted to determine a tissue oxygen saturation value (StO2) for each region, each region independent of the other regions and each region sensed using a NIRS oximeter sensor specific to that region, and determining a StO2 value for that region; b) assigning a coefficient to each region, each of which coefficients reflects a portion of the StO2 value for the region attributable to a composite venous blood return representative for the tissue regions sensed; and c) determining a composite SvO2 value for the subject using the StO2 region values and the respective coefficients. The present method is operable to determine composite SvO2 values that may be specific to several organ systems of the body, or representative of mixed venous oxygen saturation (SmvO2) or central venous oxygen saturation (ScvO2). As used herein, SmvO2 and ScvO2 are defined as types of composite venous oxygen saturation values.

According to another aspect of the present invention, an apparatus for determining a venous oxygen saturation value (SvO2) of a subject is provided. The apparatus includes a plurality of NIRS oximeter sensors and a processor. The NIRS oximeter sensors are each operable to selectively emit light at one or more predetermined wavelengths into an independent tissue region, to sense light traveling through the tissue region at the predetermined wavelengths, and to produce sensed light signals representative of the sensed light. The processor is in communication with the NIRS oximeter sensors. The processor is adapted to determine a tissue oxygen saturation value (StO2) for each region using the sensed light signals from the respective tissue region. The processor is further adapted to assign a coefficient to each region, each of which coefficients reflects a portion of the StO2 value for the region attributable to venous blood. The processor is further adapted to determine a composite SvO2 value for the subject using the StO2 region values and the respective coefficients. The processor may be further adapted to determine SmvO2 and/or ScvO2 values for the subject using the StO2 region values and the respective coefficients.

The present method and advantages associated therewith will become more readily apparent in view of the detailed description provided below, including the accompanying drawings.

DETAILED DESCRIPTION OF THE INVENTION

Figure 1:
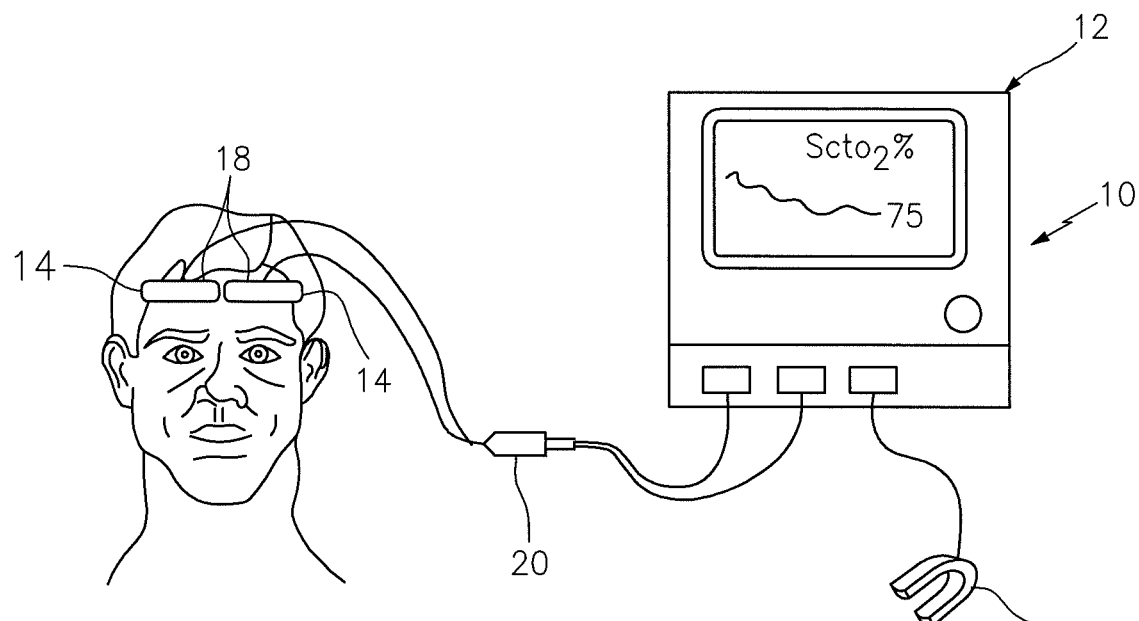
FIG. 1 is a diagrammatic illustration of an embodiment of the present invention apparatus for determining venous blood oxygen saturation levels.
Figure 2:
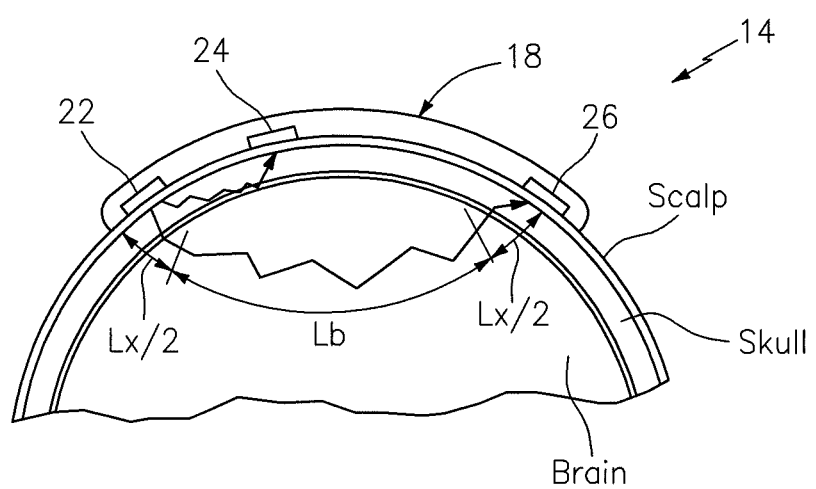
FIG. 2 diagrammatically illustrates a NIRS oximeter sensor applied to a subject's head.
Figure 3:
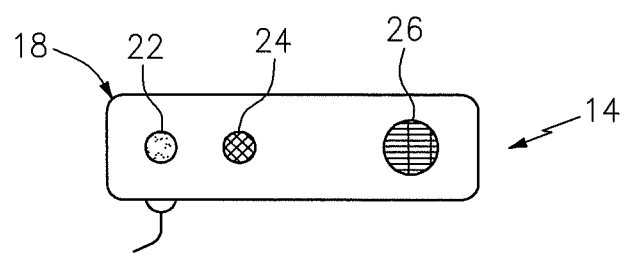
FIG. 3 diagrammatically illustrates a NIRS oximeter sensor.

Referring to FIGS. 1-3, the present invention includes an apparatus 10 and a method for determining venous blood oxygen saturation levels, which includes a processor 12 adapted in part to operate as a near infrared spectrophotometric (NIRS) oximeter operable to detect an oxygen saturation level of combined arterial and venous blood within a subject, and a NIRS sensor 14. In some embodiments, the processor 12 is also adapted to operate as a pulse oximeter operable to detect an oxygen saturation level of arterial blood within a subject, and includes a pulse oximeter sensor 16. The processor 12 is adapted to determine venous blood oxygen saturation levels using information produced using the NIRS sensor 14, and in some embodiments information produced using the pulse oximeter sensor 16 as well. A person of skill in the art will recognize that the processor may assume various forms (e.g., digital signal processor, analog device, etc.) capable of performing the functions (e.g., algorithms, sensor control, etc.) described herein.

The NIRS sensor 14 is adapted to selectively transmit light signals into the tissue of a subject and to sense the light signal once it has passed through the tissue via transmittance or reflectance. An example of an acceptable NIRS sensor 14 is diagrammatically shown in FIGS. 2 and 3. The NIRS sensor 14 includes an assembly housing 18 and a connector 20. The assembly housing 18, which is a flexible structure that can be attached directly to a subject's body, includes one or more light sources 22 and one or more light detectors 24, 26. Light is selectively emitted from the light sources 22 (e.g., laser diodes, LEDs, etc.) at predetermined wavelengths. The light sources 22 may be mounted within the assembly housing 18 or remote from the assembly housing 18, in which case the light is transferred into the sensor housing via a light pipe such as a fiber optic strand(s). One or more connector cables connect the assembly housing 18 to the processor 12. Each light detector 24, 26 includes one or more photodiodes for sensing the emitted light signals after passage through the subject's tissue, and creating light intensity signals representative of the sensed light. The photodiodes are operably connected to the processor via the connector cables. The NIRS sensors 14 diagrammatically shown in FIGS. 2 and 3 are examples of an acceptable sensor, and the present invention is not limited thereto.

Examples of acceptable NIRS oximeters and sensors are described in U.S. Pat. Nos. 6,456,862; 7,047,054; and 7,313,427, and U.S. Patent Application Publication Nos. 2009/0108205, 2009/0281403, and 2010/0049018. The present method and apparatus may be adapted to use the NIRS oximeter teachings of any and all of these publications, further modified according to the present invention. All of these published patents and applications are commonly assigned to the assignee of the present application, and all of them are hereby incorporated by reference in their entirety into the present application. The present invention is not, however, limited to the NIRS oximeters disclosed in these publications unless otherwise herein stated. Pulse oximeter algorithms and sensors are known in the prior art, and the present invention is not limited to any particular version of pulse oximeter unless otherwise stated herein.

NIRS oximetry permits non-invasive measurement of tissue oxygen saturation ($StO_2$) via a NIRS sensor placed non-invasively on the subject's skin over a tissue target area "x" (e.g., brain, skeletal muscle, liver, intestines, etc.). The NIRS sensor interrogates both venous and arterial blood of the target tissue (which tissue may include an organ) so $StO_2$ is a value between $SaO_2$ and $SvxO_2$ of the target tissue "x". For example $StO_2$ of the brain measured by NIRS has been validated against a weighted arterial and venous oxygen saturation values at a volume ratio of 30:70—30% arterial, 70% venous; e.g.: $StO_2=0.3*SaO_2+0.7*SjbO_2$, where $SjbO_2$ is brain venous blood drawn from the jugular bulb.

Figure 4:
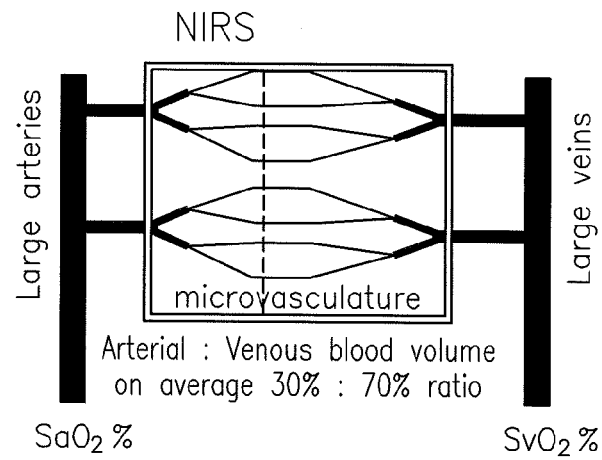
FIG. 4 is a diagrammatic illustration of microvasculature between arteries and veins.

Because NIRS technology mainly interrogates the microvasculature of tissue, which includes arterioles, venules, and capillaries as shown in FIG. 4, a NIRS tissue oxygen saturation ($StO_2$) measurement is made on a mixture of both venous and arterial blood with a mean ratio of 70% venous to 30% arterial blood volume. The venous-arterial 70/30 split has been empirically determined by PET studies for brain; e.g. See Ito et al Ann Nucl Med 2001; 15:111-6. It has been also empirically determined that the same mean ratio of 70% venous to 30% arterial blood volume applies to the whole body; e.g. see Pang C C, Measurement of body venous tone. J Pharmacol Toxicol Methods 2000; 44(2):341-60. The present invention is not limited to using a 70/30 venous/arterial split.

Figure 5:
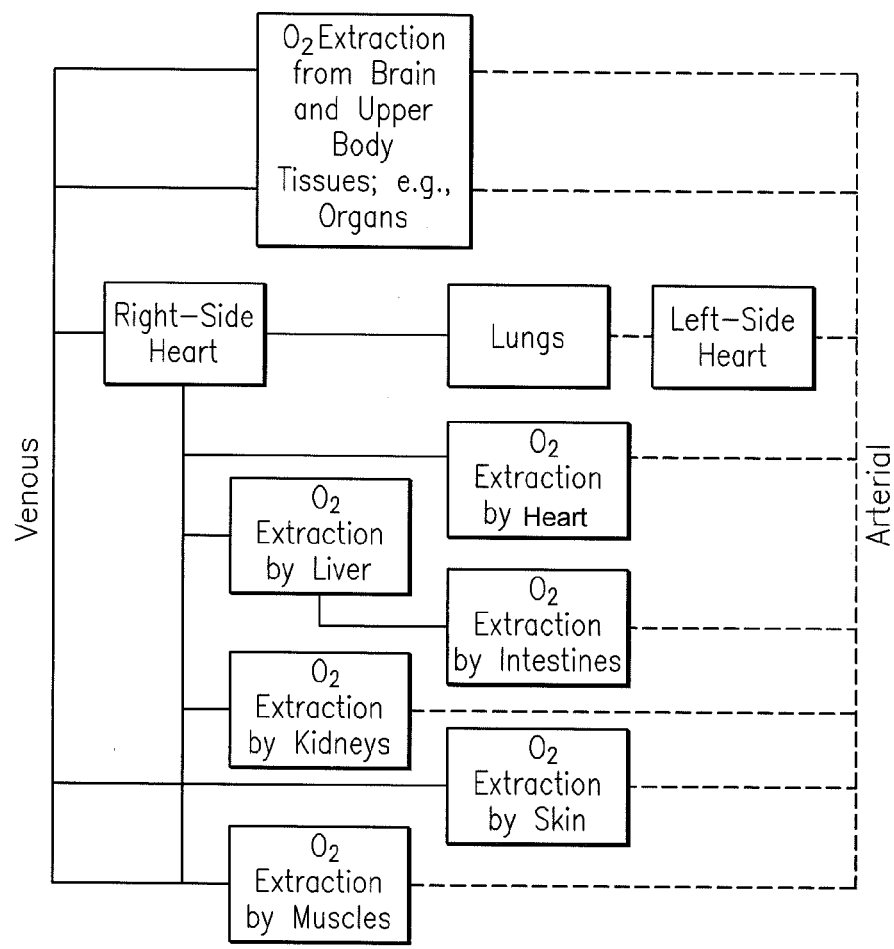
FIG. 5 is a diagram showing the arterial and venous paths within a subject, including the paths relative to certain organs and representative oxygen saturation values associated therewith.

Referring to FIG. 5, an organ receives oxygenated blood from one or more arteries. After the tissue of the organ extracts oxygen from the arterial blood for metabolism in the capillary bed, blood returns to the heart by one or more veins. Depending on the organ's metabolism level, the hemoglobin oxygen saturation of venous blood is typically relatively low and can vary depending on the particular organ; i.e., not all organs metabolize oxygen at the same rate. Smaller veins drain into larger veins via the superior vena cava (SVC) and inferior vena cava (IVC) into the heart's right atrium, then into the right ventricle, then out into the pulmonary artery where the venous blood is mixed to form "mixed" venous blood, which will have an oxygen saturation level (SmvO2) representing a mixture of individual venous oxygen saturation levels of the organs. Besides the usual organs (e.g., liver, kidneys, brain, etc.), skin and skeletal muscle metabolize significant oxygen from blood as well, because of skin and skeletal muscle's relative large mass in the body.

Referring to FIG. 5, venous blood from the different organ systems and tissues of the body travel to and are mixed in the right atrium and right ventricle of the heart. From there, they are pumped into the pulmonary artery (PA) which represents mixed venous blood. The pulmonary artery oxygen saturation ($SpaO_2$) may, therefore, be considered equivalent to the $SmvO_2$ for purposes of evaluating the various different organs; e.g., for deriving cardiac output as a mathematical function of the input venous blood oxygen saturation from the organ systems:

$$SmvO_2=SpaO_2=f(IVC, SVC) \quad \text{(Eqn. 3)}$$

Where SVC=$f$(Brain, skeletal muscle upper body and arms), and IVC=$f$(liver, intestines, kidney, skeletal muscle torso/legs). The venous blood passing through the pulmonary artery can be considered a composite venous blood because it includes blood return from a number of different regions in the body, where O2 extraction took place.

According to the present invention, "n" number of sensors are placed over "n" number of tissue regions (e.g., organs, muscles, etc.) to be evaluated, where "n" is a positive integer equal to or greater than two. The NIRS sensing data from each of these regions can be used within a function to determine a SvO2 value. For example on an adult subject, NIRS sensors could be placed on: a) the forehead for the brain; b) an arm skeletal muscle; c) a torso skeletal muscle; and d) a leg skeletal muscle, to measure their respective StO2 values. Using the NIRS sensor data from each of these tissue regions, an approximation of SvO2 can be determined by the following expression:

$$SmvO2=SpaO2=B1*StO_2 \text{ (brain)}+B2*StO_2 \text{ (arm skeletal muscle)}+B3*StO_2 \text{ (torso skeletal muscle)}+B4*StO_2 \text{ (leg skeletal muscle)} \quad \text{(Eqn. 4)}$$

The composite venous blood oxygen saturation value derived using an equation such as that shown in FIG. 4 is a composite of the venous blood saturation values of the tissue regions sensed. In the specific example of Equation 4, the tissue regions identified permit the determination of a mixed venous blood saturation value (SmvO2), which is a particular type of composite venous blood saturation value (SvO2). The coefficients "B1", "B2", "B3", and "B4" are empirically derived regression coefficients that best fit a regression line to derive SvO2 under resting conditions where skeletal muscle is not consuming large amounts of oxygen. To derive this expression, the coefficient Bn can be empirically determined from a population of similar subjects and then applied to an independent subject under test to determine SvO2 (and other data such as cardiac output) by non-invasive NIRS methods. Regression techniques are an acceptable technique for evaluating statistical data, but the present invention is not limited to using regression techniques.

The populations used to derive the empirical data, which data is used in turn to derive the coefficients, are preferably similar to that of the subject being tested; e.g., adults within a particular age range, or adolescents, or children, etc. As will be explained below, the empirical data can also be tailored to reflect smaller specific groups with which the subject may be affiliated; e.g., empirical data groups having particular disease states, or physical or social characteristics (e.g., congenital heart disease, emphysema patients, smokers, etc.).

Since liver, kidney, and intestine StO2 can be determined non-invasively by NIRS only for human subjects at a weight equal to or less than forty kilograms (40 kg), for most adults, these values cannot be measured. However for subjects at a weight equal to or less than forty kilograms (40 kg), NIRS sensors could be placed over these organs as well to derive SvO2.

To enhance the accuracy and repeatability of the venous oxygen saturation measurements, it is preferred that the measurement of a composite SvO2 must be done in a resting state, where oxygen consumption of the organ systems and skeletal muscle is proportionally a constant (i.e., the Bn values are a constant). In a more complex physiological condition, such as a disease state, the Bn values may change. If this is the case, Bn values can be derived from an independent subject population with the particular disease state.

In an alternative embodiment, the processor may be adapted to determine SvO2 values for those tissue regions where StO2 is a function of both arterial and venous oxygen saturation. Specifically, if the oxygen saturation value for arterial blood is determined (e.g., using a pulse oximeter), that value and the NIRS tissue oxygen saturation value for that region (i.e., NIRS StO2) can be used to determine the oxygen saturation value for venous blood in a particular tissue region "x":

$$\text{NIRS SvxO2} = f(\text{SaO2}, \text{NIRS StO2}) \quad \text{(Eqn. 5)}$$

In terms of a cerebral application (and using the 70/30 venous/arterial split from above), the NIRS brain SvO2 can be represented as: NIRS brain SvO2=[(NIRS brain StO2−0.3*SaO2)/0.7]. Although each organ/tissue region may metabolize oxygen at a different rate, the same approach can be applied to other organs/tissue regions using, for example, the following generic relationship:

$$\text{NIRS StO2} = Kax * \text{SaO2} + Kvx * \text{SvxO2} \quad \text{(Eqn. 6)}$$

where "Kax" represents the weighted contribution of arterial blood in the "x" tissue region, and "Kvx" represents the weighted contribution of venous blood in the "x" tissue region. This relationship assumes that SaO2 is systemic and a constant for all organ systems. Equation 6 above can be rewritten as:

$$\text{NIRS SvxO2} = (\text{StO2} - Kax * \text{SaO2})/Kvx \quad \text{(Eqn. 7)}$$

Substituting the regional venous oxygen saturation expression of Equation 7 into the SvO2 expression of Equation 4 (expressed in terms of SmvO2 here as well):

$$\begin{aligned}\text{SmvO2} = \text{SpaO2} = &B1*\text{NIRS SvxO2 (brain)} + B2*\text{NIRS} \\ &\text{SvxO2 (arm skeletal muscle)} + B3*\text{NIRS SvxO2} \\ &\text{(torso skeletal muscle)} + B4*\text{NIRS SvxO2 (leg} \\ &\text{skeletal muscle)} \end{aligned} \quad \text{(Eqn. 8)}$$

or $$\begin{aligned}\text{SmvO2} = \text{SpaO2} = &B1*[(\text{StO2}-Ka1*\text{SaO2})/Kv1] \\ &\text{(brain)} + B2*[(\text{StO2}-Ka2*\text{SaO2})/Kv2] \text{ (arm skel-} \\ &\text{etal muscle)} + B3*[(\text{StO2}-Ka3*\text{SaO2})/Kv3] \text{ (torso} \\ &\text{skeletal muscle)} + B4*[(\text{StO2}-Ka4*\text{SaO2})/Kv4] \\ &\text{(leg skeletal muscle)} \end{aligned} \quad \text{(Eqn. 9)}$$

The regional venous saturations that are used to collectively determine the mixed venous oxygen saturation (SmvO2) shown in Equations 8 and 9 (some or all of which regions could be used to determine other types of composite venous oxygen saturation values) are examples of regions that can be used, and the present invention is not limited to any particular tissue regions. For example, both SmvO2 and ScvO2 could be calculated and then compared to determine further clinical information. ScvO2 is usually measured in the superior vena cava (SVC), which contains venous blood from the upper body (brain, arm skeletal muscle, and skin). Therefore ScvO2 could be determined as a function of SVC blood (i.e., SsvcO2), separating out the upper body tissue oxygen saturation measurement from several NIRS sensors placed on the forehead (brain) and arms:

$$\text{ScvO2} = \text{SsvcO2} = B1*\text{NIRS SvxO2 (brain)} + B2*\text{NIRS} \\ \text{SvxO2 (arm skeletal muscle)}$$

or $$\text{ScvO2} = \text{SsvcO2} = B1*[(\text{StO2}-Ka1*\text{SaO2})/Kv1] \\ \text{(brain)} + B2*[(\text{StO2}-Ka2*\text{SaO2})/Kv2] \text{(arm skeletal muscle)}$$

Knowing both SmvO2 and ScvO2 and taking the difference (ScvO2−SmvO2) can provide further clinical information for certain disease states. For example, the difference between ScvO2 and SmvO2 can be used to represent only the composite of lower body NIRS StO2 measurements. However, the coefficient Bn could be different when empirically modeling ScvO2 and SmvO2 in a subject population set. Therefore the ScvO2−SmvO2 difference may be more complex, resulting in the need for both lower and upper body NIRS StO2 measurements.

Various combinations of NIRS StO2 measurement tissue regions could be used to measure a composite SvO2, and other parameters such as cardiac output. For example, in some applications, the regional tissue NIRS StO2 may be measured in one location such as from the flank or thigh muscle, with one or more NIRS sensors used in each region. In alternative applications which require more precise information (e.g., instances dictated by physiological or disease condition) NIRS StO2 measurements could be made of matching regions; e.g., left and right brain, left and right arm muscle, left and right torso muscle, left and right leg thigh or calf muscle, etc. The StO2 measurements, and SvO2 measurements based thereon, can provide clinically useful information relative to the interrogated tissue regions. Whatever combination of tissue regions is used to determine a composite SvO2, the Bn coefficient (or other statistical coefficient) could first be derived empirically on similar tissue regions within an independent subject population.

As indicated above, once a composite venous oxygen saturation SvO2 value is determined, additional data can be determined with other non-invasive or invasive measurements. For example, if an assumed or measured value for oxygen consumption ($VO_2$) is used along with SmvO2 and SaO2 values are determined, the cardiac output (CO) of the subject can be closely approximated. The oxygen content of blood (Ca and Cv) can then be defined as follows:

$$\text{Oxygen Content of blood} = [\text{Hemoglobin}] \text{ (g/dl)} \times 1.36 \\ (\text{ml } O_2/\text{g of hemoglobin}) \times \text{Saturation of} \\ \text{blood} \div 100 + 0.0032 \times \text{pressure of Oxygen (torr)}$$

Almost all oxygen in blood is bound to hemoglobin molecules in red blood cells. Measurement of the content of hemoglobin in the blood can be taken from data collected by pulse oximeters that can non-invasively measure hemoglobin content in g/dl, or by co-oximetry, or by estimation with a common value such as 12 g/dl. A Cv value can be determined via a NIRS measured SmvO2, and a Ca value can be measured via a SaO2 measurement by pulse oximetry, co-oximetry, or simply estimated with a common value such as 97%. Using the fact that each gram of hemoglobin can carry 1.36 ml of $O_2$, the oxygen content of the blood (Ca and Cv) can be estimated from the equation above so that Ca-Cv can be determined as the denominator of Equation 2.

An assumed commonly-used value for $VO_2$ at rest is 125 ml of $O_2$ per minute per square meter of body surface area. Alternatively, $VO_2$ could be measured non-invasively by using a spirometer within a closed rebreathing circuit incorporating a $CO_2$ absorber. With the aforementioned information, the CO of the subject could be then determined using Equation 2 provided above. Note that unlike the other variables to calculate cardiac output, Cv is not easily estimated or assumed. Therefore the methodology of non-invasive NIRS SmvO2 measurement using multiple sensors placed at different regions of the body described herein is desirable over an invasive pulmonary artery catheter placed inside the heart.

Although this invention has been shown and described with respect to the detailed embodiments thereof, it will be understood by those skilled in the art that various changes in form and detail may be made without departing from the spirit and scope of the invention.

What is claimed is:

1. A method for determining a venous oxygen saturation value (SvO2) of a subject, comprising the steps of:
    sensing a plurality of tissue regions on a subject using a NIRS oximeter adapted to determine a tissue oxygen saturation value (StO2) for each region, each region independent of the other regions and each region sensed using a NIRS oximeter sensor specific to that region, and each sensor having at least one light source and at least one light detector, and determining a StO2 value for that region;
    assigning a coefficient to each region, each of which coefficients reflects a portion of the StO2 value for the region attributable to a composite venous blood return representative of the tissue regions measured; and
    determining a composite SvO2 value for the subject using the StO2 region values and the respective coefficients.

2. The method of claim 1, wherein the coefficients are determined using regression techniques.

3. The method of claim 2, wherein the coefficients are determined using regression techniques applied to empirically collected data.

4. The method of claim 1, further comprising the step of determining an arterial blood oxygen saturation value (SaO2) for the subject.

5. The method of claim 4, wherein the SaO2 value is used with each regional StO2 value to determine the SvO2 value for that region.

6. The method of claim 5, wherein the regional SvO2 values are used collectively to determine at least one of a mixed venous oxygen saturation value (SmvO2) or a central venous oxygen saturation value (ScvO2) for the subject.

7. The method of claim 6, wherein the SmvO2 value and the ScvO2 value are analyzed to provide clinical information other than blood oxygen saturation.

8. The method of claim 6, further comprising the step of calculating cardiac output based on the SmvO2 value.

9. The method of claim 8, wherein the step of determining cardiac output includes utilizing independently measured $SpO_2$ and $VO_2$ values in the determination of the cardiac output.

10. The method of claim 9, wherein the SpO2 value is obtained from a pulse oximeter.

11. An apparatus for determining a venous oxygen saturation value (SvO2) of a subject, comprising:
    a plurality of NIRS oximeter sensors, each operable to selectively emit light at one or more predetermined wavelengths into an independent tissue region, and sensing light traveling through the tissue region at the predetermined wavelengths, and produce sensed light signals representative of the sensed light;
    a processor in communication with the NIRS oximeter sensors, which processor is adapted to determine a tissue oxygen saturation value (StO2) for each region using the sensed light signals from the respective tissue region, and which processor is further adapted to assign a coefficient to each region, each of which coefficients reflects a portion of the StO2 value for the region attributable to venous blood, and which processor is further adapted to determine a SvO2 value for the subject using the StO2 region values and the respective coefficients.

12. The apparatus of claim 11, wherein the coefficients are determined using regression techniques.

13. The apparatus of claim 12, wherein the coefficients are determined using regression techniques applied to empirically collected data.

14. The apparatus of claim 11, further comprising an arterial blood oxygen saturation sensor; and
    wherein the processor is adapted to determine an arterial blood oxygen saturation value (SaO2) for the subject using the arterial blood oxygen saturation sensor.

15. The apparatus of claim 14, wherein the processor is adapted to collectively use the SaO2 value and the regional StO2 values to determine at least one of a mixed venous oxygen saturation value (SmvO2) or a central venous oxygen saturation value (ScvO2).

16. The apparatus of claim 15, wherein the processor is adapted to analyze the SmvO2 value and the ScvO2 value and to produce clinical information other than blood oxygen saturation based on the analysis.

17. The apparatus of claim 15, wherein the processor is adapted to determine cardiac output based on the SmvO2 value.

18. The apparatus of claim 17, wherein the processor is adapted to determine the cardiac output using $SpO_2$ and $VO_2$ values input from independent devices.

19. The apparatus of claim 18, wherein the processor is adapted to collect the SpO2 value from a pulse oximeter.

* * * * *